United States Patent
Piron et al.

(10) Patent No.: US 10,552,582 B2
(45) Date of Patent: Feb. 4, 2020

(54) SYSTEM AND METHOD USING A COMBINED MODALITY OPTICAL PROBE

(71) Applicant: SYNAPTIVE MEDICAL (BARBADOS) INC., Bridgetown (BB)

(72) Inventors: Cameron Anthony Piron, Toronto (CA); Michael Frank Gunter Wood, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/324,434

(22) PCT Filed: Sep. 15, 2014

(86) PCT No.: PCT/CA2014/000691
§ 371 (c)(1),
(2) Date: Jan. 6, 2017

(87) PCT Pub. No.: WO2016/041046
PCT Pub. Date: Mar. 24, 2016

(65) Prior Publication Data
US 2017/0213013 A1    Jul. 27, 2017

(51) Int. Cl.
*G06F 19/00* (2018.01)
*A61B 5/00* (2006.01)

(52) U.S. Cl.
CPC ........ *G06F 19/3481* (2013.01); *A61B 5/0066* (2013.01); *A61B 5/0071* (2013.01);
(Continued)

(58) Field of Classification Search
CPC ... A61B 5/0075; A61B 5/0071; A61B 1/0638; A61B 5/0059; A61B 5/0086
(Continued)

(56) References Cited

U.S. PATENT DOCUMENTS 5,841,139 A    11/1998  Sostek et al.
6,826,424 B1 *  11/2004  Zeng ..................... G01J 3/0289
                                                            600/407
(Continued)

FOREIGN PATENT DOCUMENTS

JP    H10505167 A    5/1998
JP    2006526767 A   11/2006
(Continued)

OTHER PUBLICATIONS

Haka, Abigail S., "In vivo Margin Assessment during Partial Masectomy Breast Surgery Using Raman Spectroscopy," Cancer Res 2006; 66: (6), Mar. 15, 2006 (Year: 2006).*
(Continued)

*Primary Examiner* — Elaine Gort
*Assistant Examiner* — John P Go
(74) *Attorney, Agent, or Firm* — Perry + Currier, Inc.

(57) ABSTRACT

A system and method using a combined modality optical probe is provided. The system comprises: light source(s) providing excitation light; a first optical analysis device configured to receive light in a first range and analyze it using a first optical modality; a second optical analysis device configured to receive light in a second range and analyze it using a second optical modality slower than the first modality; an optical probe configured to: convey the excitation light to a tissue sample; receive the light in the first and second ranges from the sample; and, one or more optical conduits configured to: convey the excitation light from the light source(s) to the optical probe; convey the light in the first range from the optical probe to the first optical analysis device; and convey the light in the second range from the optical probe to the second optical analysis device.

13 Claims, 12 Drawing Sheets

(52) U.S. Cl.
CPC .......... *A61B 5/0075* (2013.01); *A61B 5/0084* (2013.01); *A61B 5/4064* (2013.01); *G06F 19/321* (2013.01); *A61B 5/0035* (2013.01)

(58) Field of Classification Search
USPC .................................. 705/2–3; 600/300–301
See application file for complete search history.

(56) References Cited

U.S. PATENT DOCUMENTS

| | | | |
|---|---|---|---|
| 7,972,272 B2 | 7/2011 | Munce et al. | |
| 8,214,010 B2 | 7/2012 | Courtney et al. | |
| 8,712,506 B2 | 4/2014 | Courtney et al. | |
| 2002/0007121 A1* | 1/2002 | Jackson | A61B 5/0059 600/475 |
| 2003/0045780 A1* | 3/2003 | Utsui | A61B 1/00167 600/182 |
| 2004/0064023 A1* | 4/2004 | Ryan | A61B 18/1492 600/374 |
| 2004/0245350 A1* | 12/2004 | Zeng | A61B 1/042 236/43 |
| 2007/0112259 A1 | 5/2007 | Tateda et al. | |
| 2008/0111080 A1* | 5/2008 | Mishin | G01V 5/0091 250/363.01 |
| 2010/0208955 A1* | 8/2010 | Mehes | G01N 21/6452 382/128 |
| 2012/0078524 A1* | 3/2012 | Stewart | A61B 5/0059 702/19 |
| 2012/0086935 A1* | 4/2012 | Smith | H04B 10/073 356/73.1 |
| 2012/0310047 A1 | 12/2012 | Kasamatsu et al. | |
| 2013/0070986 A1* | 3/2013 | Peleg | G06K 9/6254 382/128 |
| 2013/0321822 A1 | 12/2013 | Vogler et al. | |
| 2017/0213013 A1 | 7/2017 | Piron et al. | |

FOREIGN PATENT DOCUMENTS

| | | | | |
|---|---|---|---|---|
| JP | 4499354 B2 | 7/2010 | | |
| WO | WO-2005052558 A1 * | 6/2005 | ........... | A61B 5/0071 |

OTHER PUBLICATIONS

Khan, Sandra, International Search Report, PCT Patent Application No. PCT/CA2014/000691, dated Jun. 15, 2015.

AUIPO, Examination Report No. 1, dated Jun. 14, 2019, re Australian Patent Application No. 2014406558.

Kong, Kenny, et al. "Diagnosis of tumors during tissue-conserving surgery with integrated autofluorescence and Raman scattering microscopy." Proceedings of the National Academy of Sciences 110.38 (2013): 15189-15194.

Office Action dated May 31, 2018 by the Japanese Patent Office corresponding to Japanese Application No. 2017-514418.

* cited by examiner

SYSTEM AND METHOD USING A COMBINED MODALITY OPTICAL PROBE

FIELD

The present specification generally relates to automated tools for surgery, and more specifically, to a system and method for managing equipment in a medical procedure.

BACKGROUND

Brain tumors and intracranial hemorrhages (ICH) have been treated by removing most of the top half of the patient's skull and resecting healthy white matter to get to the tumor or ICH of interest. This approach has the disadvantages of: permanent removal of healthy white matter; increased trauma to the brain via de-pressurization after removal of a large portion of the skull; and long recovery time due to large cranial trauma.

The neurosurgeon can be guided in these procedures using a navigation system that displays the position of surgical tools overlaid on pre-surgical Magnetic Resonance (MR) or Computed Tomography (CT) images in real-time. In these procedures, one or more targets and a surgical path are defined. An ideal surgical path will be determined by the surgeon before the surgery but is not encoded or reflected by the navigation system.

A variety of optical techniques can be used for tissue characterization such surgeries, particularly in the context of identifying a tumour vs identifying healthy tissue. Example techniques include fluorescence techniques (with endogenous or exogenous fluorophores) including time-resolved fluorescence (fluorescence lifetime), broadband spectroscopy, Raman spectroscopy, optical coherence tomography, and numerous others. These techniques vary widely in both their sensitivity and specificity to various diseased states and also in the time and complexity of acquiring a measurement. Fluorescence and broadband spectroscopy for example can acquire an acceptable signal very rapidly (seconds or less), but generally lack specificity to tissue types, while techniques such as Raman spectroscopy require significant time to acquire an acceptable signal (30 s or more) but benefit from enhanced specificity to tissue type. As such, no one technique is ideally suited for intra-surgical analysis.

SUMMARY

This specification describes a system and method for managing equipment in a medical procedure using a combined modality optical probe which can irradiate a tissue sample with excitation light respective to two optical modalities, a first optical modality and a second optical modality that is slower than the first optical modality; the second optical modality can be more specific than the first modality. Hence, the first modality can be used as an initial screen of the tissue, and the second modality can be used when either the screen is inconclusive and/or more when more data regarding the tissue is desired.

An aspect of the specification provides a system comprising: one or more light sources configured to provide excitation light; a first optical analysis device configured to receive light in a first wavelength range and analyze the light in the first wavelength range using a first optical modality; a second optical analysis device configured to receive light in a second wavelength range and analyze the light in the second wavelength range using a second optical modality slower than the first optical modality; an optical probe configured to: convey the excitation light to a tissue sample; receive the light in the first wavelength range from the tissue sample; and receive the light in the second wavelength range from the tissue sample; and, one or more optical conduits configured to: convey the excitation light from the one or more light sources to the optical probe; convey the light in the first wavelength range from the optical probe to the first optical analysis device; and convey the light in the second wavelength range from the optical probe to the second optical analysis device.

The system can further comprise an optical coupling device configured to optically couple the optical probe to each of the one or more light sources, the first optical analysis device, and the second optical analysis device.

The system can further comprise: a computing device in communication with each of the first optical analysis device and the second optical analysis device, the computing device configured to: select the first optical modality for use at the optical probe; and, use the first optical modality as a screen of the tissue to determine whether the tissue is healthy or not healthy; and, when the screen is inconclusive: select the second optical modality for use at the optical probe; and, use the second optical modality for further interrogation of the tissue. The computing device can be further configured to use the second optical modality for further interrogation of the tissue when the tissue is determined to be at a site of interest. The computing device can be in further communication with each of the one or more light sources, the computing device further configured to select an optical modality for use by the optical probe by controlling the one or more light sources. The system can further comprise a display in communication with the computing device, the display configured to provide data relating to one or more of the first optical modality and the second optical modality.

The first optical modality can be selected from a group consisting of Ultraviolet spectroscopy, visible spectroscopy, shortwave infrared spectroscopy, near infrared spectroscopy, broadband spectroscopy, optical coherence tomography (OCT), fluorescence spectroscopy, time-resolved fluorescence spectroscopy, and laser-induced breakdown spectroscopy (LIBS).

The second optical modality can be selected from a group consisting of Raman spectroscopy, surface enhanced Raman spectroscopy (SERS), stimulated Raman spectroscopy (SRS), and coherence anti-Stokes Raman spectroscopy (CARS).

The second optical modality can have more specificity than the first optical modality.

The system can further comprise one or more power sources for powering the one or more light sources, the first optical analysis device and the second optical analysis device.

The first optical modality can be on after a computing device determines that a screen of the tissue using the first optical modality is inconclusive and the second optical modality can be intermittently used when the computing device determines that the screen of the tissue using the first optical modality is inconclusive.

Each of the one or more optical conduits can comprise one or more optical fibers.

The optical probe can comprise one or more optical fibers configured to convey the excitation light to the tissue sample and one or more further optical fibers configured to collect the light in the first wavelength range and the light in the second wavelength range from the tissue sample.

Another aspect of the specification provides a method comprising: using, at a communication device, a first optical modality as a screen of tissue to determine whether the tissue is healthy or not healthy, the computing device in communication with each of a first optical analysis device of the first optical modality and a second optical analysis device of a second optical modality slower than the first optical modality; and, when one the screen is inconclusive, using the second optical modality for further interrogation of the tissue.

The first optical modality can be on after a computing device determines that a screen of the tissue using the first optical modality is inconclusive and the second optical modality can be intermittently used when the computing device determines that the screen of the tissue using the first optical modality is inconclusive.

The method can further comprise determining whether the tissue is healthy or not healthy by: comparing one or more a collected spectrum respective to the first optical modality and collected data respective to the first optical modality to one or more of reference spectra and reference data respective to one or more of healthy tissue and unhealthy tissue; when one or more the collected spectrum and the collected data matches one or more of a healthy tissue reference spectra and healthy tissue reference data within a first given margin of error, determining that the tissue is healthy; and, when one or more the collected spectrum and the collected data matches one or more of an unhealthy tissue reference spectra and unhealthy tissue reference data within a second given margin of error, determining that the tissue is unhealthy.

The method can further comprise determining whether the screen is inconclusive by: comparing one or more a collected spectrum respective to the first optical modality and collected data respective to the first optical modality to one or more of reference spectra and reference data respective to one or more of healthy tissue and unhealthy tissue; and, when one or more the collected spectrum and the collected data does not match one or more of the reference spectra and the reference data within at least one given margin of error, determining that the screen is inconclusive.

The first optical modality can be selected from a group consisting of Ultraviolet spectroscopy, visible spectroscopy, shortwave infrared spectroscopy, near infrared spectroscopy, broadband spectroscopy, optical coherence tomography (OCT), fluorescence spectroscopy, time-resolved fluorescence spectroscopy, and laser-induced breakdown spectroscopy (LIBS).

The second optical modality can be selected from a group consisting of Raman spectroscopy, surface enhanced Raman spectroscopy (SERS), stimulated Raman spectroscopy (SRS), and coherence anti-Stokes Raman spectroscopy (CARS).

BRIEF DESCRIPTION OF THE DRAWINGS

For a better understanding of the various implementations described herein and to show more clearly how they can be carried into effect, reference will now be made, by way of example only, to the accompanying drawings in which.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein can be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the navigation method and system disclosed herein. No implementation described below limits any claimed implementation and any claimed implementations can cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein can be practiced without these specific details. In other instances, well-known methods, procedures and components have not been described in detail so as not to obscure the implementations described herein.

In this specification, elements can be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XY, YZ, ZZ, and the like). Similar logic can be applied for two or more items in any occurrence of "at least one . . . " and "one or more . . . " language.

Figure 1:
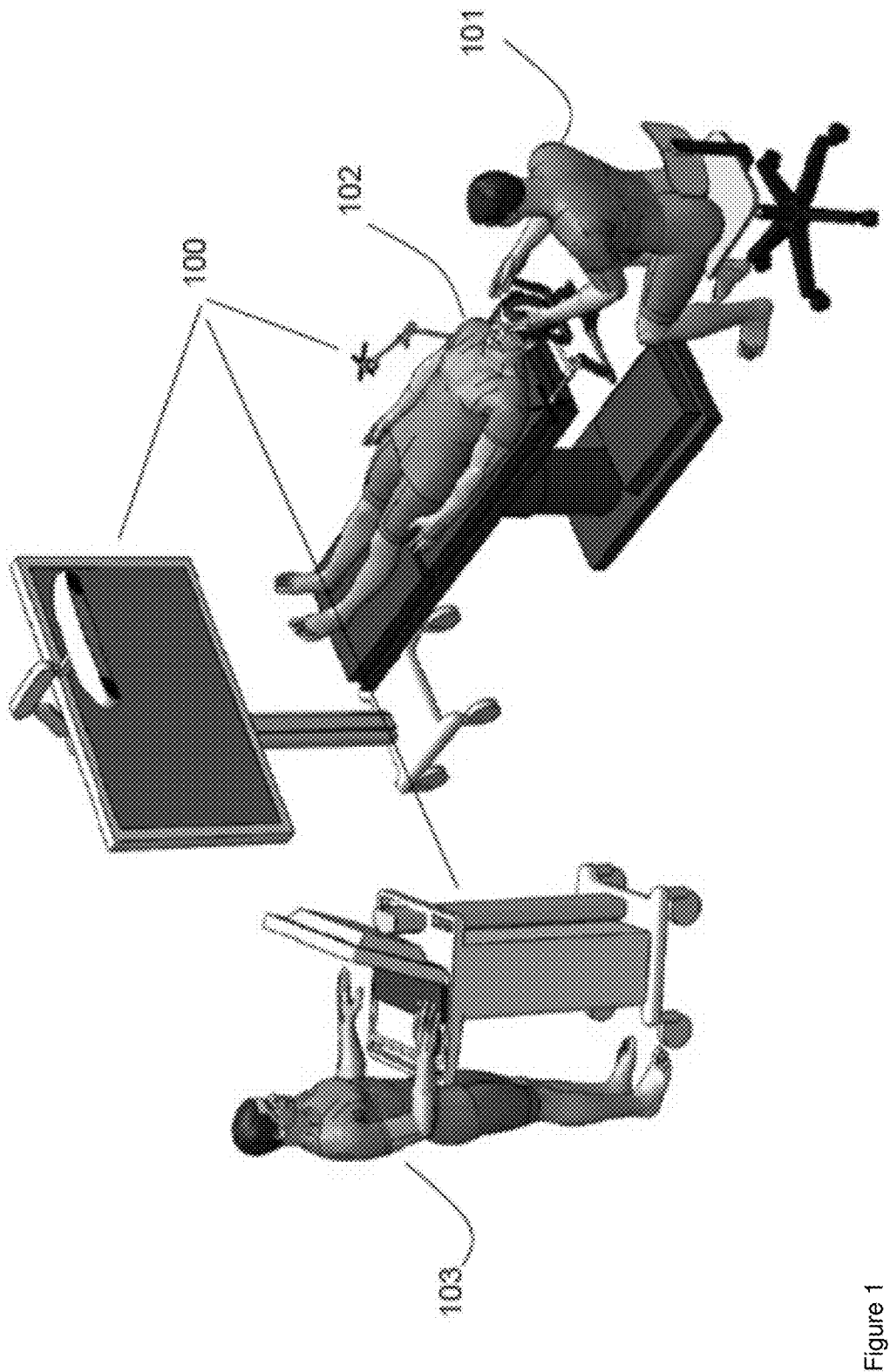
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 can also be present to operate, control and provide assistance for the navigation system 100.

Figure 2:
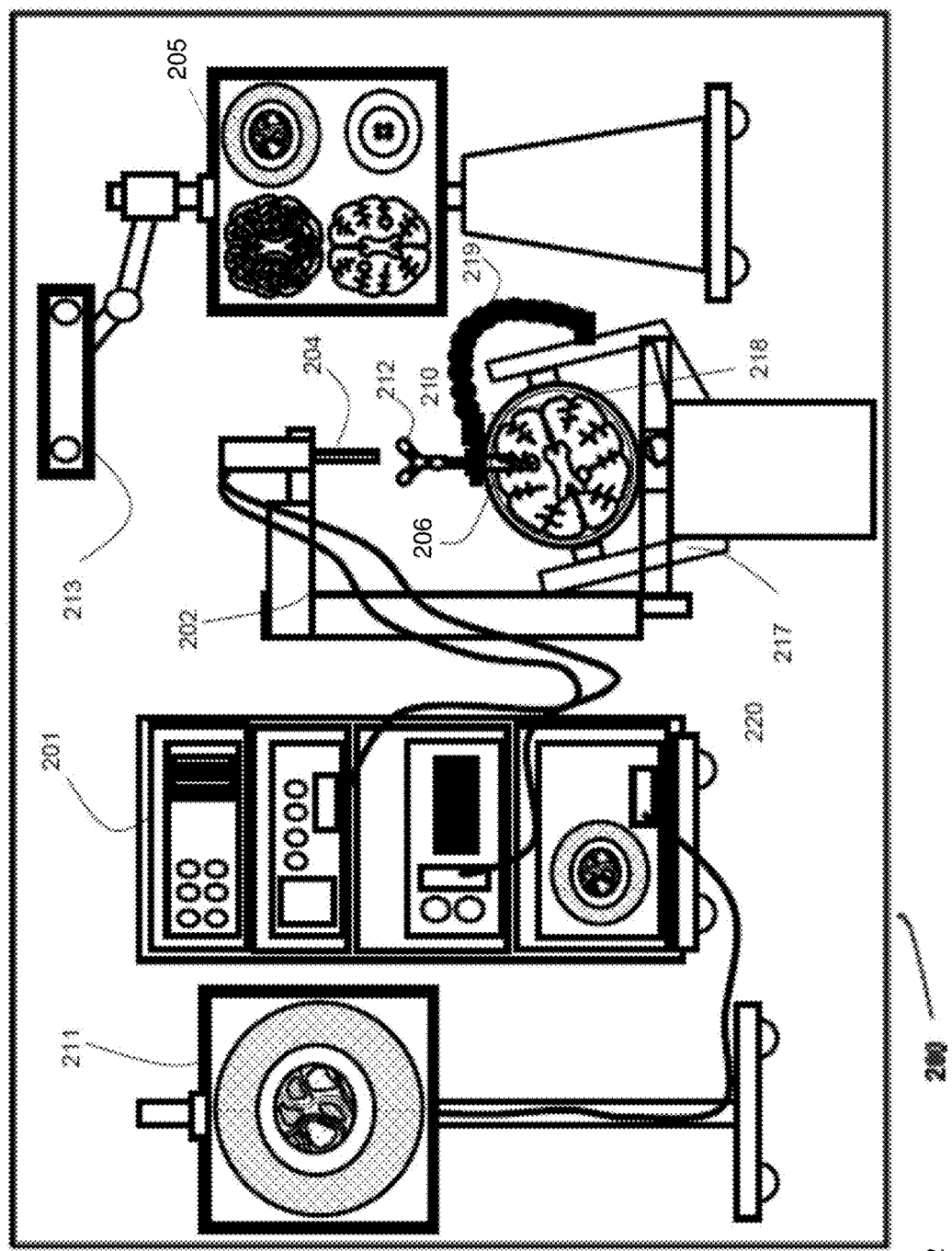
FIG. 2 is a block diagram illustrating components of a medical navigation system that can be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, can be implemented. The medical navigation system 200 includes, but is not limited to, one or more monitors 205, 211 for displaying a video image, an equipment tower 201, and a mechanical arm 202, which supports an optical scope 204. The equipment tower 201 can be mounted on a frame (e.g., a rack or cart) and can contain a computer or controller (examples provided with reference to FIGS. 3 and 6 below), planning software, navigation software, a power supply and software to manage the mechanical arm 202, and tracked instruments. In one example non-limiting implementation, the equipment tower 201 can comprise a single tower configuration with dual display monitors 211, 205, however other configurations can also exist (e.g., dual tower, single display, etc.). Furthermore, the equipment tower 201 can also be configured with a universal power supply (UPS) to provide for emergency power, in addition to a regular AC adapter power supply.

A patient's anatomy can be held in place by a holder. For example, in a neurosurgical procedure the patient's head can be held in place by a head holder 217, and an access port 206 and an introducer 210 can be inserted into the patient's head. The introducer 210 can be tracked using a tracking camera 213, which provides position information for the navigation system 200. The tracking camera 213 can also be used to track tools and/or materials used in the surgery, as described in more detail below. In one example non-limiting implementation, the tracking camera 213 can comprise a 3D (three-dimensional) optical tracking stereo camera, similar to one made by Northern Digital Imaging (NDI), configured to locate reflective sphere tracking markers 212 in 3D space. In another example, the tracking camera 213 can comprise a magnetic camera, such as a field transmitter, where receiver coils are used to locate objects in 3D space, as is also known in the art. Location data of the mechanical arm 202 and access port 206 can be determined by the tracking camera 213 by detection of tracking markers 212 placed on these tools, for example the introducer 210 and associated pointing tools. Tracking markers can also be placed on surgical tools or materials to be tracked. The secondary display 205 can provide output of the tracking camera 213. In one example non-limiting implementation, the output can be shown in axial, sagittal and coronal views as part of a multi-view display.

As noted above with reference to FIG. 2, the introducer 210 can include tracking markers 212 for tracking. The tracking markers 212 can comprise reflective spheres in the case of an optical tracking system and/or pick-up coils in the case of an electromagnetic tracking system. The tracking markers 212 can be detected by the tracking camera 213 and their respective positions are inferred by the tracking software.

As shown in FIG. 2, a guide clamp 218 (or more generally a guide) for holding the access port 206 may be provided. The guide clamp 218 can optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 can be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
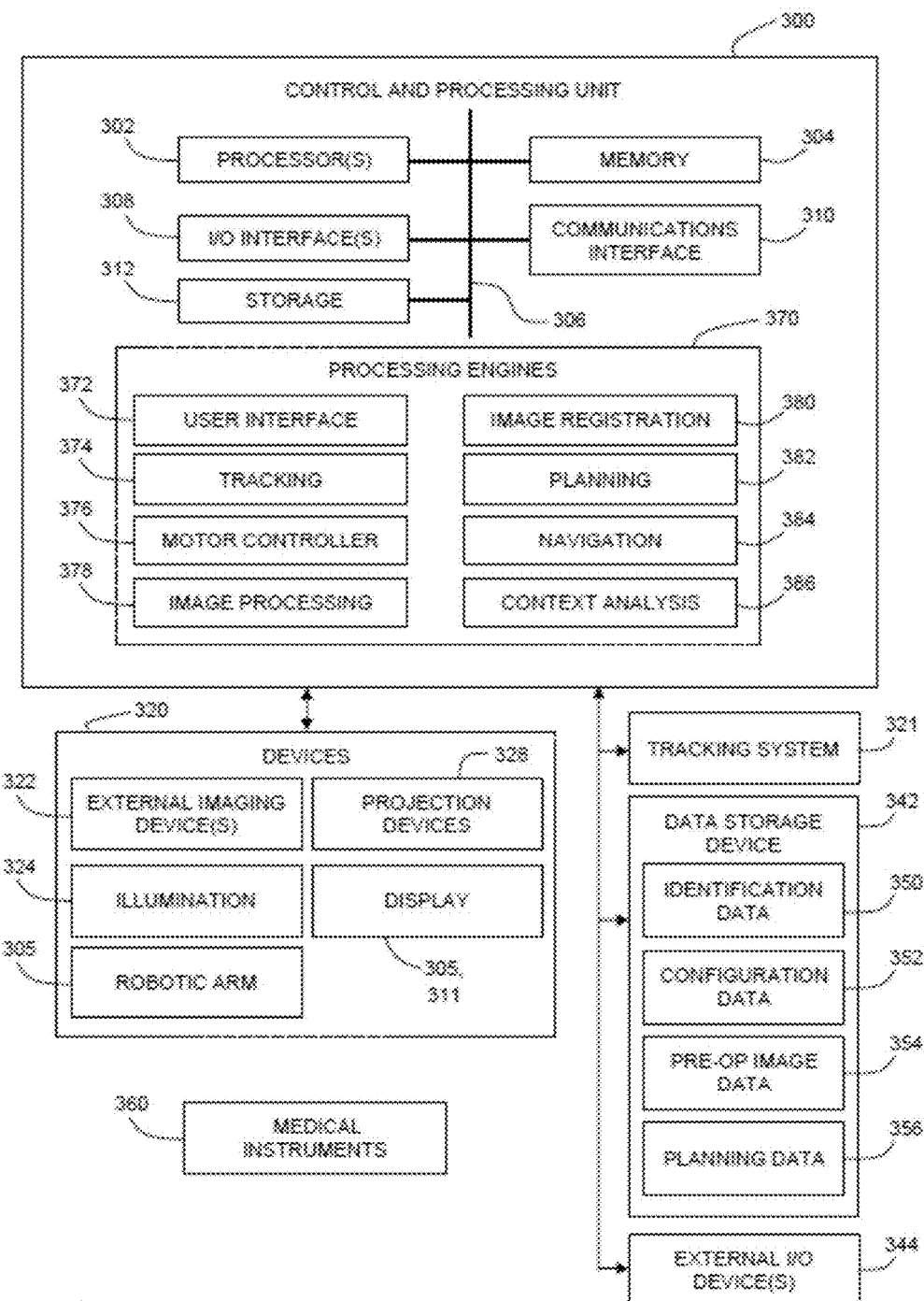
FIG. 3 depicts a block diagram illustrating components of a planning system used to plan a medical procedure that can then be implemented using the navigation system of FIG. 2, according to non-limiting implementations.

Referring to FIG. 3, a block diagram is shown illustrating a control and processing unit 300 that can be used in the navigation system 200 of FIG. 2 (e.g., as part of the equipment tower). In one example non-limiting implementation, control and processing unit 300 can include one or more processors 302, a memory 304, a system bus 306, one or more input/output interfaces 308, a communications interface 310, and storage device 312. In particular, one or more processors 302 can comprise one or more hardware processors and/or one or more microprocessors. Control and processing unit 300 can be interfaced with other external devices, such as tracking system 321, data storage device 342, and external user input and output devices 344, which can include, but is not limited to, one or more of a display, keyboard, mouse, foot pedal, and microphone and speaker. Data storage device 342 can comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 can also include, but is not limited to, preoperative image data 354 and/or medical procedure planning data 356. Although data storage device 342 is shown as a single device in FIG. 3, in other implementations, data storage device 342 can be provided as multiple storage devices.

Medical instruments 360 can be identifiable using control and processing unit 300. Medical instruments 360 can be connected to and controlled by control and processing unit 300, and/or medical instruments 360 can be operated and/or otherwise employed independent of control and processing unit 300. Tracking system 321 can be employed to track one or more of medical instruments 360 and spatially register the one or more tracked medical instruments 360 to an intraoperative reference frame. In another example, a sheath can be placed over a medical instrument 360 and the sheath can be connected to and controlled by control and processing unit 300.

Control and processing unit 300 can also interface with a number of configurable devices, and can intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification can be implemented via processor(s) 302 and/or memory 304. For example, the functionalities described herein can be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 can be stored in the memory 304 and the processing modules can be collectively referred to as processing modules 370.

It is to be understood that the system is not intended to be limited to the components shown in FIG. 3. One or more components of the control and processing unit 300 can be provided as an external component or device. In one example non-limiting implementation, navigation engine 384 can be provided as an external navigation system that is integrated with control and processing unit 300.

Some implementations can be implemented using processor 302 without additional instructions stored in memory 304. Some implementations can be implemented using the instructions stored in memory 304 for execution by one or more general purpose microprocessors. Thus, the specification is not limited to a specific configuration of hardware and/or software.

While some implementations can be implemented in fully functioning computers and computer systems, various implementations are capable of being distributed as a computing product in a variety of forms and are capable of being applied regardless of the particular type of machine or computer readable media used to actually effect the distribution.

At least some aspects disclosed can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, can be used to store software and data which, when executed by a data processing system, causes the system to perform various methods. The executable software and data can be stored in various places including for example ROM, volatile RAM, nonvolatile memory and/or cache. Portions of this software and/or data can be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical and/or other forms of propagated signals, such as carrier waves, infrared signals, digital signals, and the like. The storage medium can comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium can be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions can also be in various forms, including compiled and non-compiled code.

According to one aspect of the present application, one purpose of the navigation system 200, which can include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification can be applied to other suitable medical procedures.

Figure 4:
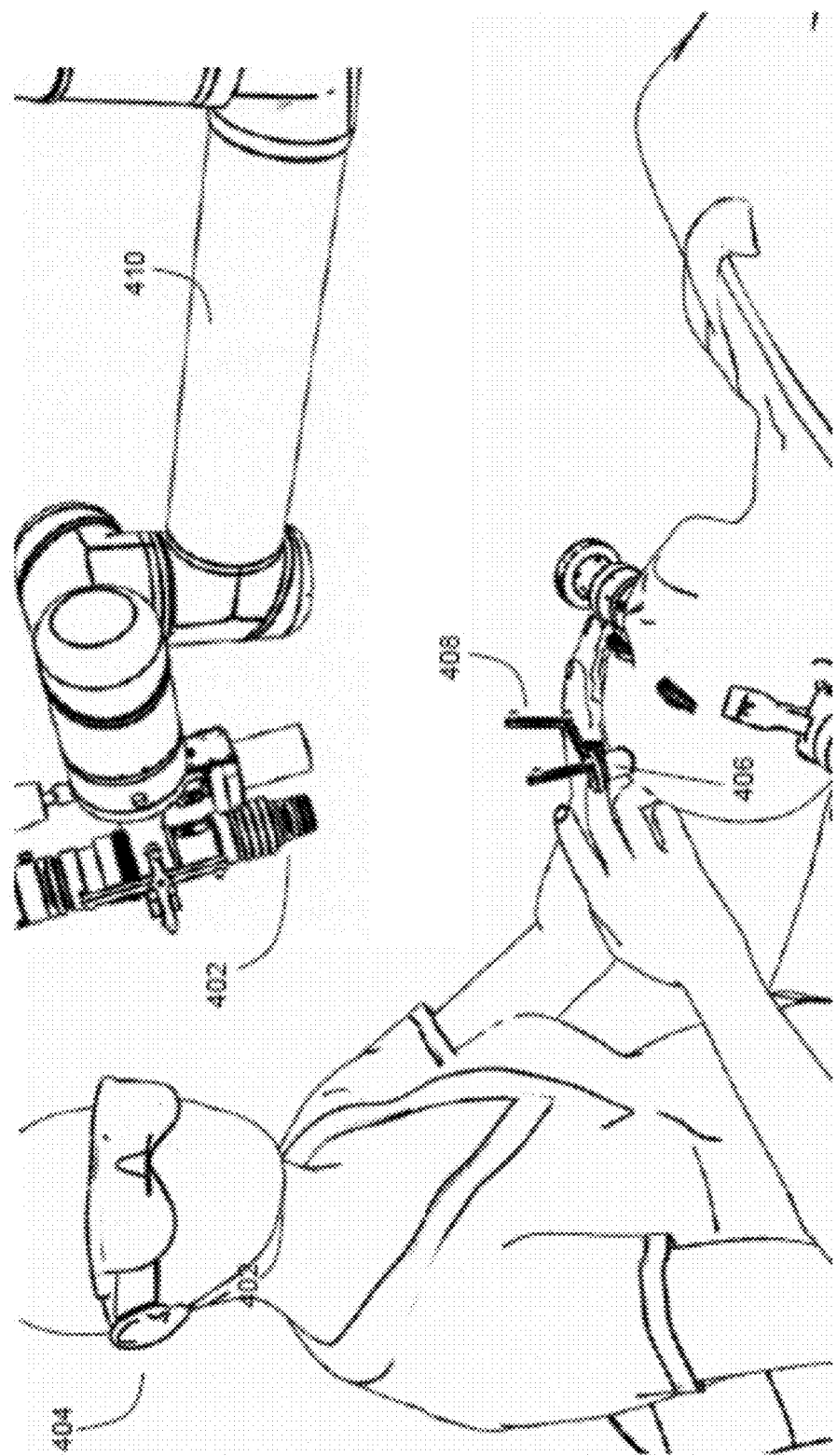
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, can align video scope 402 to peer down port 406. Video scope 402 can be attached to an adjustable mechanical arm 410. Port 406 can have a tracking tool 408 attached to it where tracking tool 408 is tracked by a tracking camera of a navigation system.

Even though the video scope 402 can comprise an endoscope and/or a microscope, these devices introduce optical and ergonomic limitations when the surgical procedure is conducted over a confined space and conducted over a prolonged period such as the case with minimally invasive brain surgery.

Figure 5:
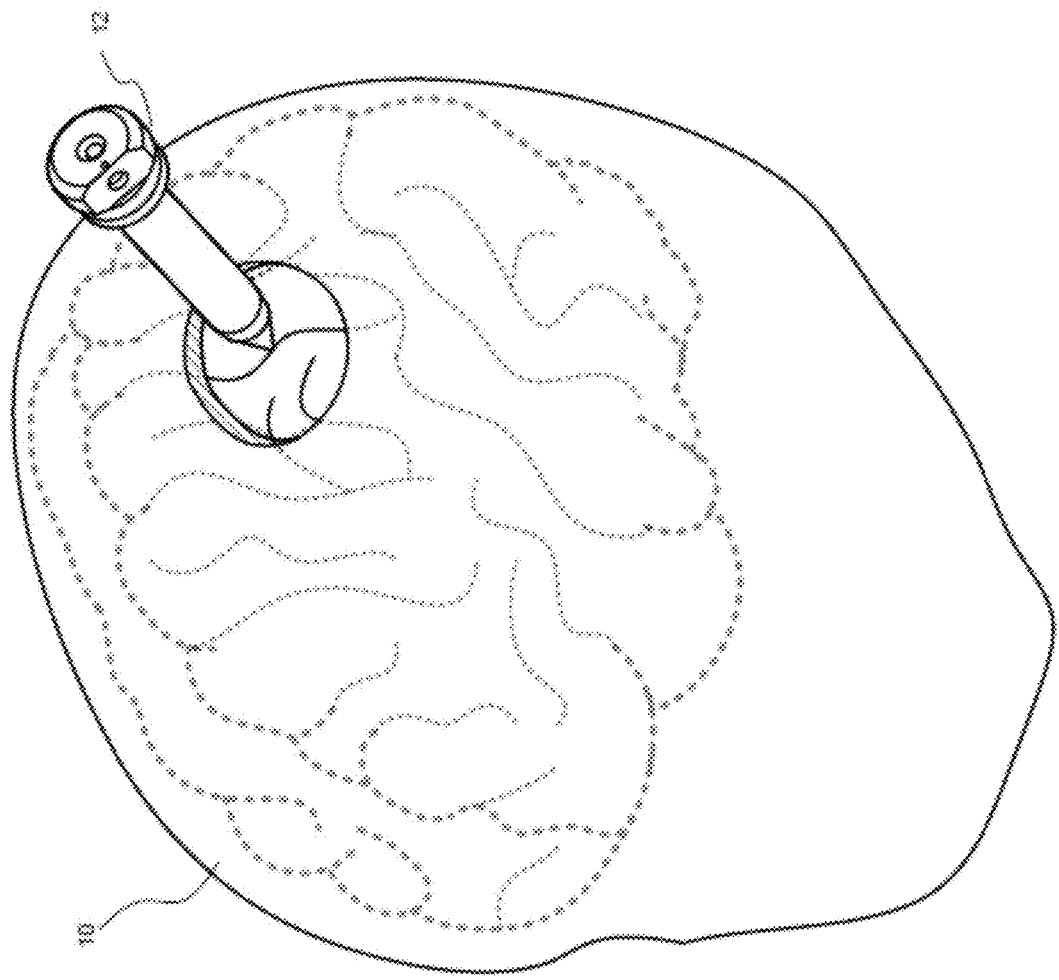
FIG. 5 depicts insertion of an access port into a human brain, for providing access to internal brain tissue during a medical procedure, according to non-limiting implementations.

FIG. 5 illustrates the insertion of an access port 12 into a human brain 10, in order to provide access to internal brain tissue during a medical procedure. In FIG. 5, access port 12 is inserted into a human brain 10, providing access to internal brain tissue. Access port 12 can include, but is not limited to, instruments such as catheters, surgical probes, and/or cylindrical ports such as the NICO BrainPath. Surgical tools and instruments can then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments would then be inserted down the access port 12.

Attention is next directed to FIGS. 6 through 12, which depict apparatus, systems and methods related to a combined modality optical probe, according to non-limiting implementations. Specifically, the described combined modality optical probe can be used for tissue analysis, and can offer a number of advantages. Specifically, the described combined modality optical probe enables the use of two optical analysis devices when characterizing tissue. For example, UV/VIS (ultraviolet/visible) fluorescence (e.g., one or more of tissue autofluorescence, exogenous fluorphores and PPIX (Protoporphyrin IX) fluorescence) could be combined with NIR (near infrared) Raman spectroscopy in a single probe, as each modality is sufficiently separated in wavelength. Because of this, a probe capable of measuring both fluorescence and Raman signals can be realized according to the present specification, assuming the fluorescence and Raman wavelengths are sufficiently separated such that they do not interfere with each other (as is the case with UV/visible fluorescence and 785 nm Raman). The combined modality optical probe could split the measured light into two separate optical fibers and each to respective optical excitation and measurements systems for fluorescence and Raman. A similar combined modality optical probe could also be utilized for combined broadband UV/visible and Raman spectroscopy, provided the broadband spectroscopy does not interfere with the Raman. Such modality optical probe could be integrated into a resection or suction tool and probe could be tracked as part of the surgical navigation system.

Figure 6:
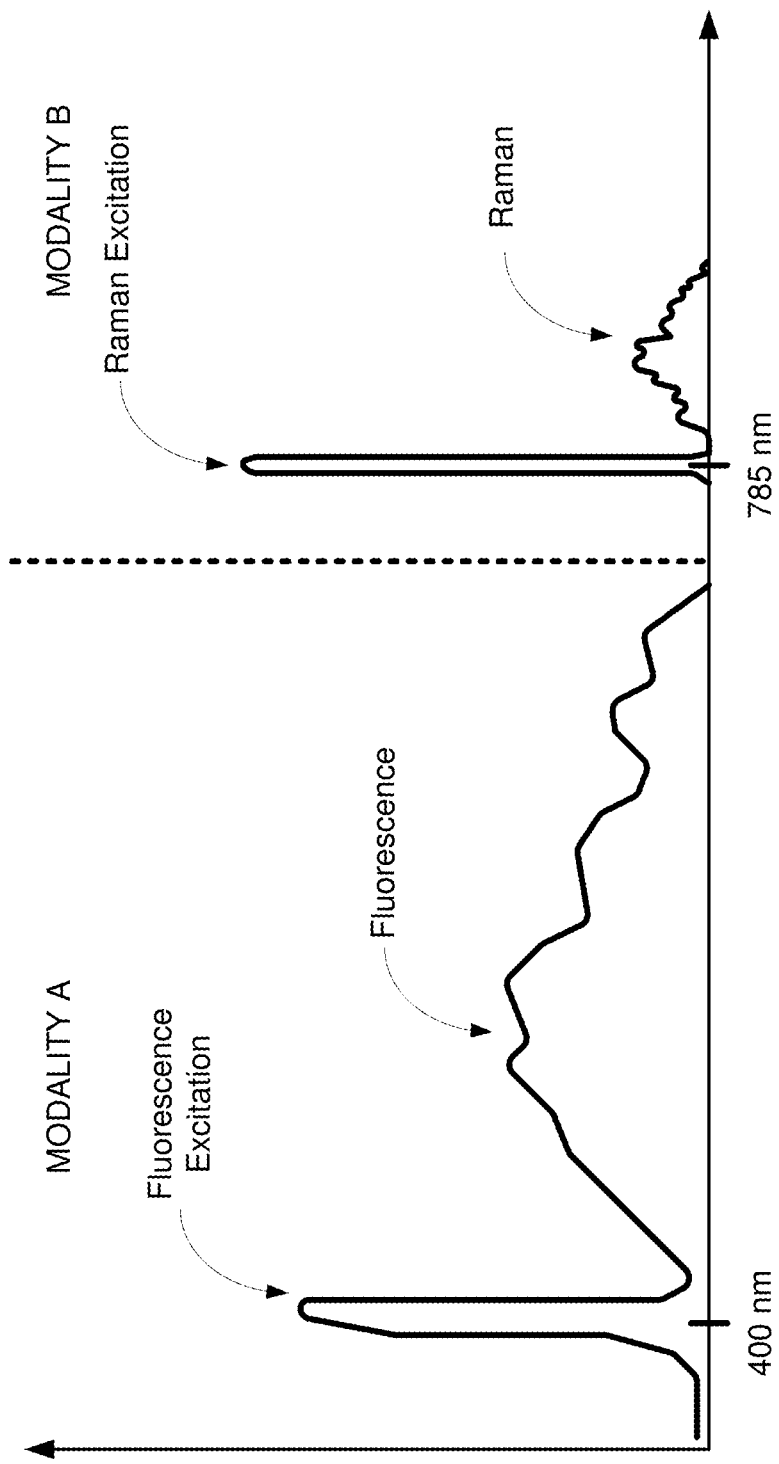
FIG. 6 depicts example spectra showing two optical modalities, according to non-limiting implementations.

For example, attention is next directed to FIG. 6 which depicts a non-limiting example spectrum of two optical modalities: "Modality A" which, as depicted, comprises fluorescence spectroscopy, and "Modality B" which, as depicted, comprises Raman spectroscopy. In particular, the spectrum of FIG. 6 depicts intensity vs. wavelength of the two different modalities that are "sufficiently" separated. In particular, the spectrum, shows fluorescence excitation light at about 400 nm and Raman excitation light at about 785 nm, and the resulting spectra for each modality, i.e. a fluorescence spectrum of light that results from a sample (for example a tissue sample) being exposed to the fluorescence excitation light and a Raman spectrum of light that results from the sample being exposed to the Raman excitation light. "Sufficiently" separated can be understood to mean that the there is little and/or no overlap between each spectrum and/or no overlap between the excitation light of the higher wavelength and the spectrum in the lower wavelength range. In yet further implementations, "sufficiently" separated can be understood as excitation light of one modality (e.g. Raman) has a higher wavelength than the highest wavelength of the spectrum of the other modality (e.g. fluorescence) and/or where there is some overlap (e.g. a small portion of the fluorescence spectrum is present at 785 nm), the spectrum of the other modality is below a threshold value and/or in a range that is not measured by an analysis device. However, in other implementations, the spectra of each modality can overlap at least to some degree, and light respective to each modality can be filtered out using suitable optical and/or dichroic filters.

From FIG. 6, it is further apparent that the spectrum of Modality A, as depicted is, larger in magnitude than the spectrum of Modality B, however the spectrum of Modality B can have more data encoded therein, and/or be more specific to a type of tissue being exposed to both excitation wavelengths.

In other words, one of the modalities can be faster than the other modality, and/or have a faster acquisition time, as the respective spectrum is larger in magnitude, while the other modality can provide more and/or better data as to the nature of the tissue being irradiated and/or tested.

For example, the fluorescence signal is larger in magnitude than the Raman signal and hence the fluorescence signal can be acquired quickly, relative to the Raman spectrum, for example in less than about a second, and hence can be understood as a "fast" modality; however fluorescence is not as sensitive to changes in a sample, relative to Raman, and hence lacks specificity relative to Raman. In contrast, the Raman signal is low in magnitude, relative to the fluorescence signal, and hence the Raman signal is acquired slowly, for example in greater than or equal to about ten seconds, relative to acquisition of the fluorescence spectrum, and hence can be understood as a "slow" modality; however, Raman is more specific than fluorescence in that differences in Raman signals from healthy and unhealthy (e.g. cancerous) tissue are greater than differences in fluorescence signals from healthy and unhealthy tissue. Hence, both modalities can be used to characterize tissue, as described herein, with the quicker, but less specific, modality used more often (i.e. UV fluorescence) then the slower, but more specific, modality (i.e. Raman). Specificity, as described herein, can also be referred to as sensitivity.

Hence, a system where both modalities are available using a combined modality optical probe, as described hereafter, could be used in the following ways:

1) The modality with the faster acquisition time (e.g. fluorescence or broadband) could be as a "first line" measurement to determine tissue state/type. A more sensitive but more time consuming second optical modality (e.g. Raman) could be used when the result of the "first line" measurement was inconclusive (i.e. result had an unacceptably high probability of error, where unacceptably high is understood to be above a threshold probability of error) and/or a tissue site being tested was of particular interest. The "first line" measurement could be performed in real-time and/or close to real-time to guide a resection, and, upon an uncertain measurement, the surgery could temporarily pause (for less than one minute) while a longer Raman measurement was made.

2) The combination of the two modalities could also be used to for better predictive capabilities than either modality has on its own. For example, fluorescence spectroscopy and Raman spectroscopy probe different chemical properties of tissue; hence, a combination of the two measurements on a sample could provide a more specific measurement of tissue state (e.g. healthy or unhealthy/cancerous) as the strengths and/or advantages of each modality will be available.

Figure 7:
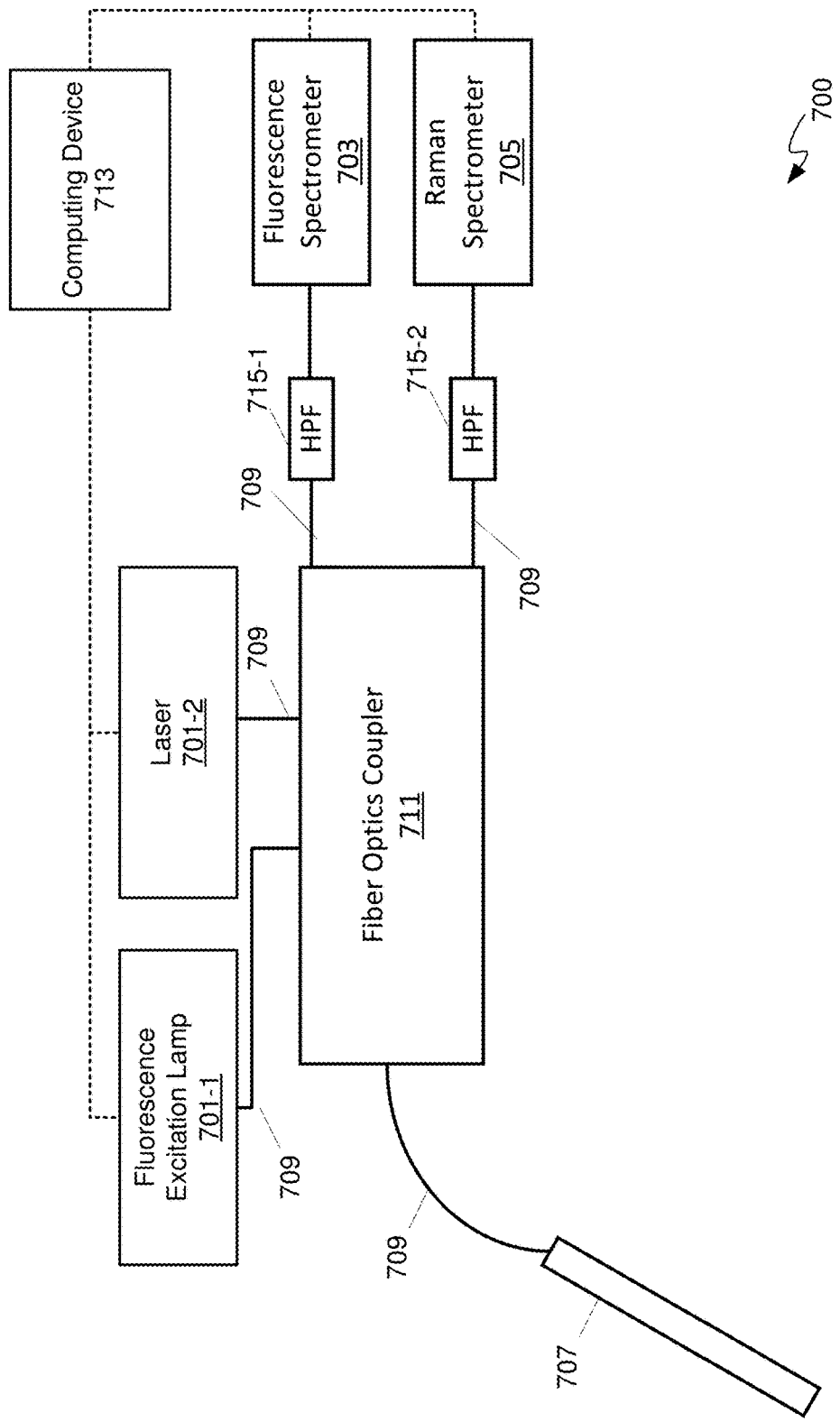
FIG. 7 depicts a system that includes a combined optical modality probe and optical analysis devices respective to two optical modalities, according to non-limiting implementations.

Attention is next directed to FIG. 7, which depicts a system 700 comprising: one or more light sources 701-1, 701-2 (interchangeably referred to hereafter, collectively, as light sources 701 and generically as a light source 701) configured to provide excitation light; a first optical analysis device 703 configured to receive light in a first wavelength range and analyze the light in the first wavelength range using a first optical modality; a second optical analysis device 705 configured to receive light in a second wavelength range and analyze the light in the second wavelength range using a second optical modality slower than the first optical modality; an optical probe 707 configured to: convey the excitation light to a tissue sample; receive the light in the first wavelength range from the tissue sample; and receive the light in the second wavelength range from the tissue sample; and, one or more optical conduits 709 configured to: convey the excitation light from the one or more light sources 701 to the optical probe 707; convey the light in the first wavelength range from the optical probe 707 to the first optical analysis device 703; and convey the light in the second wavelength range from the optical probe 707 to the second optical analysis device 705.

As depicted, system 700 further comprises an optical coupling device 711 configured to optically couple the optical probe 707 to each of the one or more light sources 701, the first optical analysis device 703, and the second optical analysis device 705. For example, each of the optical conduits 709 can comprise one or more optical fibers, and optical coupling device 711 can comprise an optical fiber coupling device. Specifically, as depicted, the optical probe 707 is optically coupled to the optical coupling device 711 using one bundle of optical fibers, and optical coupling device 711 couples various optical fibers from the optical probe 707 to each of the one or more light sources 701, the first optical analysis device 703, and the second optical analysis device 705, as described in further detail below.

As depicted system further comprises: computing device 713, which can be similar to the control and processing unit described above with reference to FIG. 3. Computing device 713 can be in communication with each of the first optical analysis device 703 and the second optical analysis device 705 and, optionally each of the light sources 701. In FIG. 1, electrical communication and/or electrical data paths are depicted as stippled lines to distinguish them from the optical conduits 709.

In general, computing device 713 can be configured to: select a first optical modality for use at the optical probe 707; and, use the first optical modality as a screen of tissue (e.g. being probed by the optical probe 707) to determine whether the tissue is healthy or not healthy; and, when the screen is inconclusive: select the second optical modality for use at the optical probe 707; and, use the second optical modality for further interrogation of the tissue. In some implementations, the computing device 713 is further configured to use the second optical modality for further interrogation of the tissue when the tissue is determined to be at a site of interest. In yet further implementations, the computing device can be in further communication with each of the one or more light sources 701, the computing device 713 further configured to select an optical modality for use by the optical probe by controlling the one or more light sources 701, for example by turning each of the light sources 701 on and off.

While not depicted, system 700 can further comprise a display, similar to displays 305, 311, in communication with the computing device 713, the display configured to provide data relating to one or more of the first optical modality and the second optical modality.

While also not depicted, system 700 can further comprise one or more power sources for powering the one or more light sources 701, the first optical analysis device 703 and the second optical analysis device 705.

As depicted, system 700 further comprises a first high pass filter (HPF) 715-1 configured to filter out light outside of an analysis range of the first optical analysis device 703, and a second high pass filter (HPF) 715-2 configured to filter out light outside of an analysis range of the second optical analysis device 705. High pass filters 715-1, 715-2 are interchangeably referred to hereafter, collectively, as high pass filters 715 and generically as a high pass filter 715. Furthermore, each high pass filter 715 can comprise a band pass filter which allows a band of light frequencies to pass there through, filtering out frequencies outside the band. Each high pass filter 715 is located along a respective optical conduit 709 between at least the optical probe 707 and each of the first optical analysis device 703 and the second optical analysis device 705, and can comprise a dichroic filter, and the like, configured to transmit wavelengths either above a given wavelength and/or in a given wavelength range to filter out least respective excitation wavelengths, as described in further detail below.

While the first optical analysis device 703 is depicted, and described herein, as a fluorescence spectrometer, the first optical analysis device 703 can have an optical modality that is selected from a group consisting of Ultraviolet spectroscopy, visible spectroscopy, shortwave infrared spectroscopy, near infrared spectroscopy, broadband spectroscopy, optical coherence tomography (OCT), fluorescence spectroscopy, time-resolved fluorescence spectroscopy, and laser-induced breakdown spectroscopy (LIBS).

Similarly, while the second optical analysis device 705 is depicted, and described herein, as a Raman spectrometer, the second optical analysis device 705 can have an optical modality that is selected from a group consisting of Raman spectroscopy, surface enhanced Raman spectroscopy (SERS), stimulated Raman spectroscopy (SRS), and coherence anti-Stokes Raman spectroscopy (CARS). In other words, the second optical modality (e.g. the optical modality of the second optical analysis device 705) of system 700 is slower, but can have better specificity, than the first optical modality (e.g. the optical modality of the first optical analysis device 703) of system 700.

As already noted, in specific non-limiting implementations depicted in FIG. 7, the first optical analysis device 703 comprises a fluorescence spectrometer, and the second optical analysis device 705 comprises a Raman spectrometer. Hence, the first light source 701-1 can comprise a light source compatible with the fluorescence spectrometer and/or the first light source 701-1 is configured to produce excitation light for inducing a fluorescence spectrum in tissue; in such implementations, the first light source 701-1 comprises a light source configured to produce light at about 400 nm. Similarly, the second light source 701-2 can comprise a light source compatible with the Raman spectrometer and/or the second light source 701-2 is configured to produce excitation light for inducing a Raman spectrum in tissue; in such implementations, the second light source 701-2 comprises a light source, including, but not limited to a laser, configured to produce light at about 785 nm. However, each light source 701 can be adapted to each of the first optical analysis device 703 and the second optical analysis device 705, and can depend on the modality of each.

In implementations, wherein the first and second modality comprise, respectively, fluorescence spectrometry and Raman spectrometry, high pass filter 715-1 filters out light below about 450 nm and/or transmits light above about 450 nm and/or transmits light in an analysis range of fluorescence spectrometry, including, but not limited to about 450 nm to about 700 nm; similarly, in these implementations, high pass filter 715-2 filters out light below about 790 nm and/or transmits light above about 790 nm and/or transmits light in an analysis range of Raman spectrometry, including, but not limited to above about 790 nm. However, each of high pass filters 715-1, 715-2 can be adapted to each of the first optical analysis device 703 and the second optical analysis device 705, and can depend on the modality of each.

Furthermore, while light sources 701 are depicted as separate devices, in yet further implementations light sources 701 can be combined in one device configured to emit excitation light respective to both optical modalities.

The optical probe 707 comprises a combined optical modality optical probe and is configured to: irradiate a sample, including, but not limited to tissue, with excitation light from each of the one or more light sources 701, and collect light respective to each of the optical modalities. In general, the optical probe 707 comprises a body, a connection end, configured to connect with one or more respective optical conduits 709, (and the connection end can hence comprise one or more optical connectors), and an opposing sample-interaction end, as well optical components that convey light between the ends. For example, the optical probe 707 can comprise one or more optical fibers configured to convey excitation light to a tissue sample and one or more further optical fibers configured to collect light in a first wavelength range, respective to the first optical modality, and light in second wavelength range, respective to the second optical modality, from the tissue sample.

Furthermore, the optical probe 707 has dimensions compatible with an access port, such as access port 12, with which the optical probe 707 is to be used. For example, the optical probe 707 has a diameter and/or a largest transverse dimension, and the like that is less than an inner diameter of an access port, and can have a length that is greater than a length the access port. In some implementations, the optical probe 707 has a diameter, and the like, that is less than about ⅓ of an inner diameter of an access port with which the optical probe 707 is to be used.

In addition, the optical probe 707 can be circular in cross-section, though the optical probe 707 need not be circular in cross-section. For example, the optical probe 707 can be triangular, square, pentagonal, hexagonal, etc., in cross-section and/or irregular in cross-section.

Figure 8:
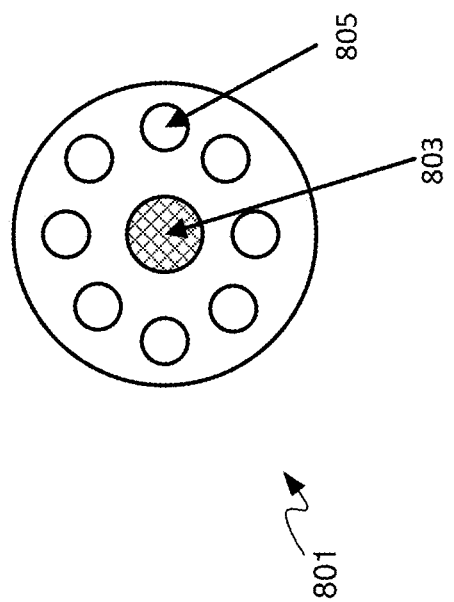
FIG. 8 depicts an end and/or a cross-section of the combined optical modality probe of FIG. 7, according to non-limiting implementations.
Figure 9:
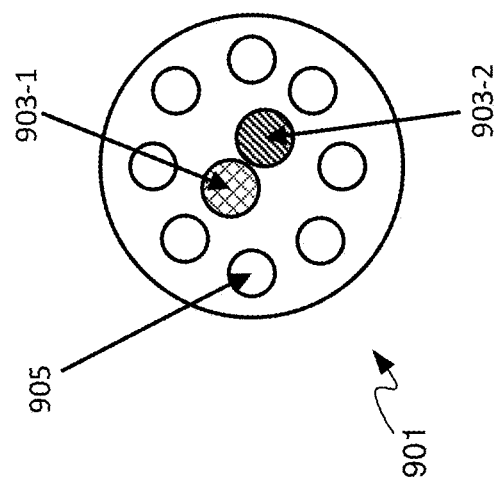
FIG. 9 depicts an end and/or a cross-section of the combined optical modality probe of FIG. 7, according to alternative non-limiting implementations.
Figure 10:
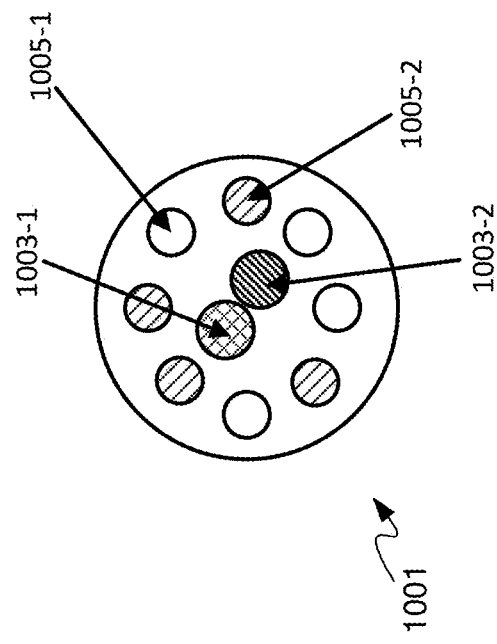
FIG. 10 depicts an end and/or a cross-section of the combined optical modality probe of FIG. 7, according to alternative non-limiting implementations.

Attention is directed to FIG. 8, which depicts a sample-interaction end 801 of the optical probe 707 according to some non-limiting implementations. The sample interaction end 801 comprises an end opposite a respective optical conduit 709 between the optical probe 707 and at least light sources 701, first optical analysis device 703 and second optical analysis device 705, and/or optical coupling device 711. As the optical probe 707 can be generally cylindrical, the sample-interaction end 801 can have the same configuration as a transverse cross-section of the optical probe 707.

In any event, in non-limiting implementations depicted in FIG. 8, the sample-interaction end 801 and/or transverse cross-section, comprises a excitation fiber optic 803 and/or fiber optic bundle, that conveys excitation light from light sources 701 to a sample, the excitation fiber optic 803 optionally located (as depicted) at about a center of optical probe 707; in other words, excitation fiber optic 803 is in optical communication with one or more optical conduits 709 between the optical probe 707 and the light sources 701.

The excitation fiber optic 803 can be located at about a center of the sample-interaction end 801 and/or the transverse cross-section.

Furthermore, as depicted, the sample interaction end 801, and/or transverse cross-section, comprises a plurality of collection fiber optics 805 (only one of which is indicated in FIG. 8 for clarity) arranged around the excitation fiber optic 803, the plurality of collection fiber optics 805 configured to convey light emitted from a sample irradiated with the excitation light to each of the first optical analysis device 703 and the second optical analysis device 705. In other words, the plurality of collection fiber optics 805 is in optical communication with one or more optical conduits 709 between the optical probe 707 and each of the first optical analysis device 703 and the second optical analysis device 705.

While not depicted, the sample-interaction end 801 can further comprise one or more lenses, microlenses, prisms, mirrors and/or other optical devices configured to one or more of focus excitation light, collect emitted light, and/or steer and/or bend excitation light and/or emitted light to and from a region of interest.

While FIG. 8 depicts eight collection fiber optics 805 optionally arranged circularly around the excitation fiber optic 803, the present specification can include fewer than eight and more than eight collection fiber optics 805, which can be arranged with circular symmetry or no symmetry. For example, in other implementations, the sample interaction end 801, and/or transverse cross-section can comprise one collection fiber optic 805 located adjacent an excitation fiber optic, which need be located at a center of the sample interaction end 801.

Other optical configurations of the optical probe are within the scope of present implementations. For example, attention is next directed to FIG. 9 which depicts an alternative non-limiting implementation of another sample-interaction end 901 of the optical probe 707. The sample-interaction end 901 is substantially similar to the sample-interaction end 801, with like elements having like numbers, but starting with a "9" rather than an "8". In particular, the sample-interaction end 901 comprises a first excitation fiber optic 903-1 and a second excitation fiber optic 903-2. The first excitation fiber optic 903-1 in optical communication with the first light source 701-1, and is configured to that convey excitation light from the first light source 701-1 to a sample. Similarly, the second excitation fiber optic 903-2 in optical communication with the second light source 701-2, and is configured to that convey excitation light from the second light source 701-2 to a sample. Hence, each of the first excitation fiber optic 903-1 and the second excitation fiber optic 903-2 is in optical communication with a respective optical conduit 709 to respectively each of the first light source 701-1 and the second light source 701-2. Furthermore, each of the first excitation fiber optic 903-1 and the second excitation fiber optic 903-2 can be adjacent to one another and generally centrally located in the optical probe 707.

The sample-interaction end 901 further comprises a plurality of collection fiber optics 905 that are similar to collection fiber optics 805. Further, the depicted sample-interaction end 901 can also be representative of a cross-section of the optical probe 707, similar to the sample-interaction end 801.

Other optical configurations of the optical probe are within the scope of present implementations. For example, attention is next directed to FIG. 10 which depicts an alternative non-limiting implementation of another sample-interaction end 1001 of the optical probe 707. The sample-interaction end 1001 is substantially similar to the sample-interaction end 901, with like elements having like numbers, but starting with a "10" rather than a "9". For example, the sample-interaction end 1001 comprises a first excitation fiber optic 1003-1, similar to first excitation fiber optic 903-1, and a second excitation fiber optic 1003-2, similar to second excitation fiber optics 903-2. However, in contrast to the sample-interaction end 901, the sample-interaction end 1001 comprises a first set of collection fiber optics 1005-1 and a second set of collection fiber optics 1005-2, which are arranged around excitation fiber optics 1003-1, 1003-2, in configurations similar to collection fiber optics 803, 903 described above, however a first set of collection fiber optics 1005-1 is in optical communication with the first optical analytical device 703, via a respective optical conduit 709, and the second set of collection fiber optics 1005-2 is in optical communication with the second optical analytical device 705, via another optical conduit 709.

As the second optical modality of system 700 can be slower than the first optical modality, the second set of collection fiber optics 1005-2 can comprise more fiber optics than the first set of collection fiber optics 1005-1 though, as depicted, the number of each of the first and second set of collection fiber optics 1005-1, 1005-2 are the same.

Further, the depicted sample-interaction end 1001 can also be representative of a cross-section of the optical probe 707, similar to the sample-interaction 801.

In particular, as optical fibers in the sample-interaction ends 901, 1001 can be dedicated to one modality or another modality, the respective optical fibers can be configured specifically for a respective modality. For example, optical fibers 903-1, 1003-1, can be configured to convey light of about 400 nm, when the first optical modality comprises fluorescence spectroscopy, while optical fibers 903-2, 1003-2 can be configured to convey light of about 785 nm when the second optical modality comprises Raman spectroscopy; similarly optical fibers 1005-1 can be configured to convey light in range of about 450 nm to about 700 nm, when the first optical modality comprises fluorescence spectroscopy, while optical fibers 1005-2 can be configured to convey light above about 790 nm when the second optical modality comprises Raman spectroscopy. Respective optical conduits 709 can be similarly configured. Further, each set of optical fibers depicted in FIGS. 8-10, as well as respective optical conduits 709, can be adapted based on which modalities are used in system 700 and/or wavelengths of light that each set of optical fibers is to convey.

Figure 11:
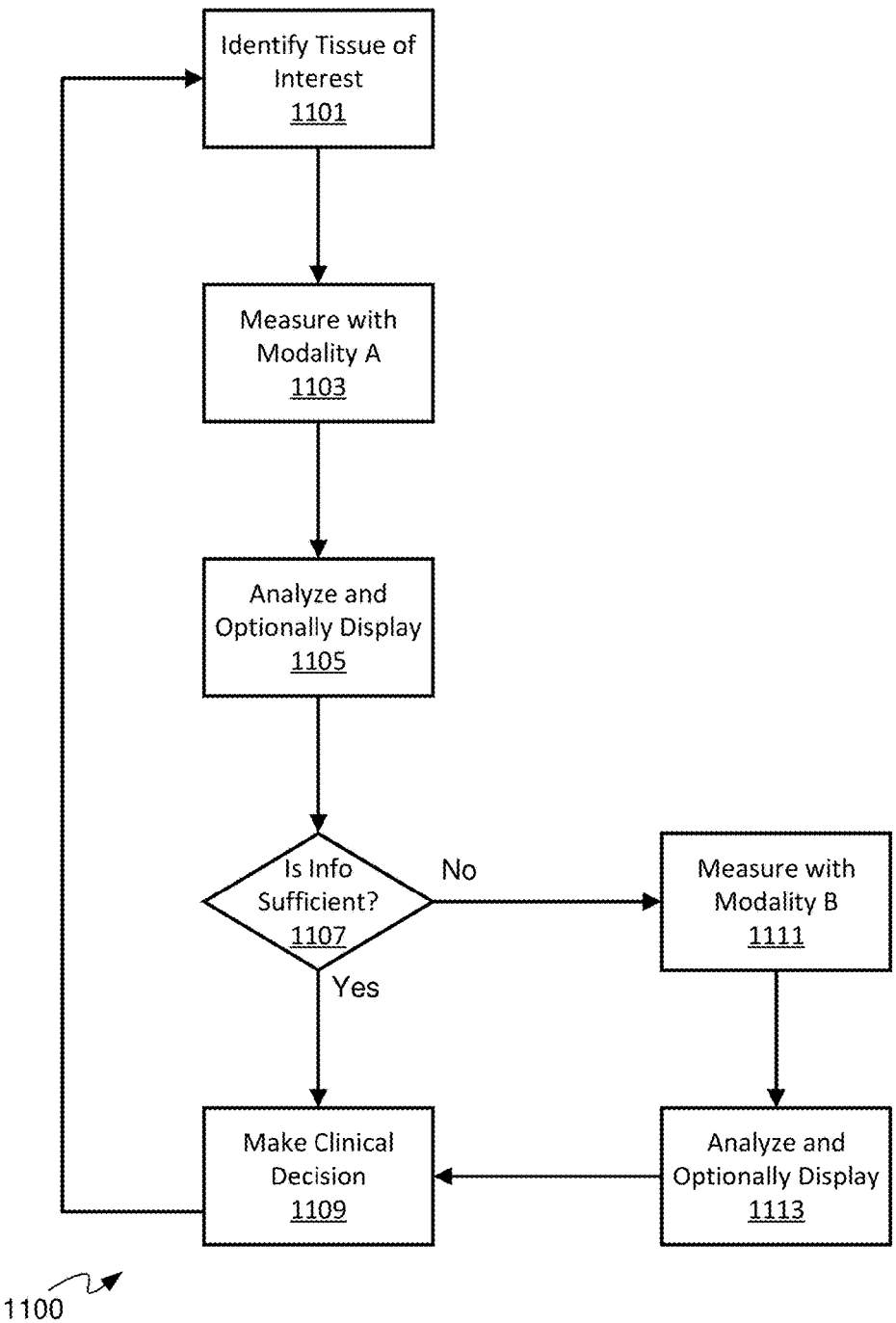
FIG. 11 depicts a method for operating a combined modality optical probe, according to non-limiting implementations.

Attention is now directed to FIG. 11 which depicts a flowchart of a method 1100 for operating a combined modality optical probe, according to non-limiting implementations. In order to assist in the explanation of method 1100, it will be assumed that method 1100 is performed using system 700. Furthermore, the following discussion of method 1100 will lead to a further understanding of system 700 and its various components. However, it is to be understood that system 700 and/or method 1100 can be varied, and need not work exactly as discussed herein in conjunction with each other, and that such variations are within the scope of present implementations.

In some implementations, method 1100 is implemented in system 700 at least partially by a processor of computing device 713. Indeed, method 1100 is one way in which computing device 713 can be configured.

Regardless, it is to be emphasized, that method 1100 need not be performed in the exact sequence as shown, unless otherwise indicated; and likewise various blocks may be performed in parallel rather than in sequence; hence the elements of method 1100 are referred to herein as "blocks" rather than "steps". It is also to be understood, however, that method 1100 can be implemented on variations of system 700 as well.

At block 1101 a tissue of interest is identified. For example, a tissue of interest can be identified by positioning the optical probe 707 in the access port 12, and indicating to computing device 713 that the tissue proximal the optical probe 707 is tissue of interest.

At block 1103, the tissue of interest is measured with a first optical modality, referred to in FIG. 11 as "Modality A". For example the computing device 713 can control the light source 701-1 to turn on so that the tissue of interest is irradiated with excitation light associated with a first optical modality, and the computing device 713 can control the first optical analysis device 703 to collect a spectrum from the tissue of interest via the optical probe 707. In other words, light in a first wavelength range associated with the first optical modality is collected by the optical probe 707 from the tissue of interest and is conveyed to the first optical analysis device 703.

At block 1105, the measurements of the first optical analysis device 703 are analyzed, for example at one or more of the computing device 713 and the first optical analysis device 703, and optionally displayed at a display of system 700.

At block 1107 it is determined whether the information collected by the first optical analysis device 703 is "sufficient"; for example, the collected spectrum and/or collected data can be compared to a reference spectrum and/or reference data associated with healthy tissue and/or the collected spectrum and/or collected data can be compared to a reference spectrum and/or reference data associated with unhealthy (e.g. cancerous) tissue.

When a determination can be made that the tissue of interest is healthy or not healthy (i.e. a "Yes" decision at block 1107), a clinical decision can be made at block 1109, for example to remove unhealthy tissue or to not remove healthy tissue. Such a determination can be made when the collected spectrum and/or collected data matches a respective reference spectrum and/or respective reference data of healthy tissue or unhealthy tissue within a given margin of error. Method 1100 then repeats: for example a surgeon, and the like can move the optical probe 707 to a new position within the access port 12 so that new tissue of interest is identified at block 1101.

However, returning to block 1107, when a determination cannot be made that the tissue of interest is healthy or not healthy (i.e. a "No" decision at block 1107, e.g. when the collected spectrum and/or collected data does not match a respective reference spectrum and/or respective reference data of healthy tissue or unhealthy tissue within a given margin of error), at block 1111 the tissue of interest is measured with a second optical modality, referred to in FIG. 11 as "Modality B". For example the computing device 713 can control the light source 701-2 to turn on so that the tissue of interest is irradiated with excitation light associated with a second optical modality, and the computing device 713 can control the second optical analysis device 705 to collect a spectrum from the tissue of interest via the optical probe 707. In other words, light in a second wavelength range associated with the second optical modality is collected by the optical probe 707 from the tissue of interest and is conveyed to the second optical analysis device 705. It is appreciated that, as the second optical modality is slower than the first optical modality, block 1111 can take a longer time to implement than block 1103.

At block 1113, the measurements of the second optical analysis device 705 are analyzed, for example at one or more of the computing device 713 and the first second analysis device 705, and optionally displayed at a display of system 700. As the second optical modality can provide better specificity than the first optical modality, at block 1109 a clinical decision can be made using the additional information and/or data obtained by the second optical modality, for example based on whether the tissue of interest is healthy or not healthy. Similar to the determination made with regard to data collected in the first optical modality, such a determination can be made by determining whether the collected spectrum and/or collected data in the second optical modality matches a respective reference spectrum and/or respective reference data, respective to the second optical modality, of healthy tissue or unhealthy tissue within a given margin of error.

Again, after block 1109, method 1100 can repeat, as described above.

Figure 12:
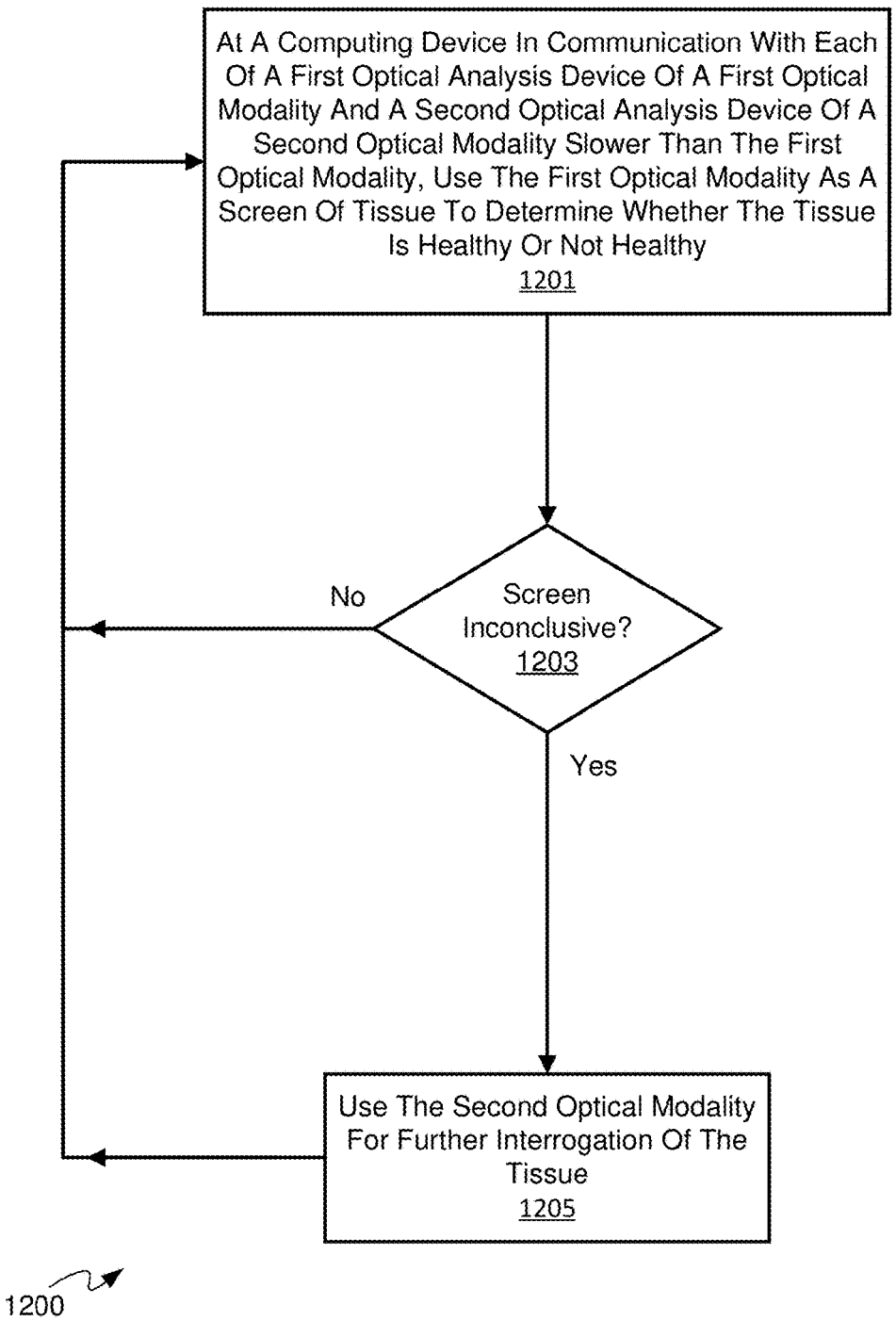
FIG. 12 depicts a method for operating a combined modality optical probe, according to non-limiting implementations.

A simplified alternative to method 1100 can also be implemented, as depicted in FIG. 12. Specifically, to FIG. 11 which depicts a flowchart of a method 1200 for operating a combined modality optical probe, according to non-limiting implementations. In order to assist in the explanation of method 1200, it will be assumed that method 1200 is performed using system 700. Furthermore, the following discussion of method 1200 will lead to a further understanding of system 700 and its various components. However, it is to be understood that system 700 and/or method 1200 can be varied, and need not work exactly as discussed herein in conjunction with each other, and that such variations are within the scope of present implementations.

In some implementations, method 1200 is implemented in system 700 at least partially by a processor of computing device 713. Indeed, method 1200 is one way in which computing device 713 can be configured.

Regardless, it is to be emphasized, that method 1200 need not be performed in the exact sequence as shown, unless otherwise indicated; and likewise various blocks may be performed in parallel rather than in sequence; hence the elements of method 1200 are referred to herein as "blocks" rather than "steps". It is also to be understood, however, that method 1200 can be implemented on variations of system 700 as well.

At block 1201, at computing device 713 in communication with each of the first optical analysis device 703 of a first optical modality and the second optical analysis device 705 of a second optical modality slower than the first optical modality, use the first optical modality as a screen of tissue to determine whether the tissue is healthy or not healthy. For example, as described above, the computing device 713 can cause the first light source 701-1 to turn on so that the optical probe 707 irradiates the tissue with excitation light respective to the first optical modality, and cause the first optical analysis device 703 to collect resulting light emitted and/or reflected from the tissue as collected by the optical probe 707.

At block 1203, it is determined whether the screen is conclusive or inconclusive. For example, block 1203 can further comprise determining whether the tissue is healthy or not healthy by: comparing one or a collected spectrum respective to the first optical modality and collected data respective to the first optical modality to one or more of reference spectra and reference data respective to one or more of healthy tissue and unhealthy tissue; when one or more the collected spectrum and the collected data matches one or more of a healthy tissue reference spectra and healthy tissue reference data within a first given margin of error, determining that the tissue is healthy; and, when one or more the collected spectrum and the collected data matches one or more of an unhealthy tissue reference spectra and unhealthy tissue reference data within a second given margin of error, determining that the tissue is unhealthy.

Similarly, block 1203 can further comprise determining whether the screen is inconclusive by: comparing one or more a collected spectrum respective to the first optical modality and collected data respective to the first optical modality to one or more of reference spectra and reference data respective to one or more of healthy tissue and unhealthy tissue; when one or more the collected spectrum and the collected data does not match one or more of the reference spectra and the reference data within at least one given margin of error, determining that the screen is inconclusive.

When one the screen is inconclusive (i.e. a "Yes" decision at block 1203), at block 1205, the second optical modality is used for further interrogation of the tissue. For example, as described above, the computing device 713 can cause the second light source 701-2 to turn on so that the optical probe 707 irradiates the tissue with excitation light respective to the second optical modality, and cause the second optical analysis device 705 to collect resulting light emitted and/or reflected from the tissue as collected by the optical probe 707.

Method 1200 can then be repeated from block 1201. Otherwise, when the screen using the first optical modality is conclusive (i.e. a "No" decision at block 1203), method 1200 can be repeated at block 1201, and block 1205 is skipped.

In some implementations, of method 1200, and/or method 1100, the first optical modality can always be on at the optical probe 707, and the second optical modality is on only when the computing device 713 determines that a screen of the tissue using the first optical modality is inconclusive. In other words, the first light source 701-1 can also be on so that excitation light respective to first optical modality always irradiates the tissue using the optical probe 707. The second optical modality is only used (i.e. the second light source 701-2 is turned on and the second optical analysis device 705 used) when the screen at block 1203 is inconclusive, as described above.

In any event, described herein is a system and method for managing equipment in a medical procedure using a combined modality optical probe which can irradiate a tissue sample with excitation light respective to two optical modalities, a first optical modality and a second optical modality that is slower than the first optical modality; the second optical modality can be more specific than the first modality. Hence, the first modality can be used as an initial screen of the tissue, and the second modality can be used when either the screen is inconclusive and/or more when more data regarding the tissue is desired.

While the applicant's teachings described herein are in conjunction with various implementations for illustrative purposes, it is not intended that the applicant's teachings be limited to such implementations. On the contrary, the applicant's teachings described and illustrated herein encompass various alternatives, modifications, and equivalents, without departing from the implementations, the general scope of which is defined in the appended claims. Except to the extent necessary or inherent in the processes themselves, no particular order to steps or stages of methods or processes described in this specification is intended or implied. In many cases the order of process steps can be varied without changing the purpose, effect, or import of the methods described.

What is claimed is:

1. A system comprising:
one or more light sources configured to provide excitation light including a first light source configured to emit light in a first wavelength range and a second light source configured to emit light in a second wavelength range;
a first optical analysis device configured to receive light in the first wavelength range and analyze the light in the first wavelength range using a first optical modality;
a second optical analysis device configured to receive light in the second wavelength range and analyze the light in the second wavelength range using a second optical modality, the first optical modality having a faster acquisition time than the second optical modality, the second optical modality providing at least one of more detailed data and data with higher specificity, as compared to the first optical modality, regarding a nature of tissue under analysis during surgery using the first optical analysis device and the second optical analysis device;
an optical probe positioned to identify a region of interest, the optical probe configured to: convey the excitation light to tissue; receive the light in the first wavelength range from the tissue; and receive the light in the second wavelength range from the tissue;
a sample-interaction end of the optical probe comprising: excitation fiber optics configured to convey the excitation light from the one or more light sources to the optical probe; a first set of fiber optics configured to convey the light in the first wavelength range from the optical probe to the first optical analysis device; and a second set of fiber optics configured to convey the light in the second wavelength range from the optical probe to the second optical analysis device, a number the second set of fiber optics being more than a respective number of the first set of fiber optics;
a display device; and,
a computing device in communication with each of the first optical analysis device and the second optical analysis device, the one or more light sources, and the display device, the computing device configured to, during the surgery and when the optical probe is positioned to identify the region of interest:
control the first light source to be on and the second light source to be off;
screen the tissue according to the first optical modality using the first optical analysis device;
when the screen of the tissue using the first optical modality is determined to be inconclusive wherein the computing device is further configured to determine that the screen is inconclusive when a measurement of the tissue using the first optical modality has a margin of error that is above a threshold margin of error:
control the first light source to remain on;
control the second light source to be on, such that the second optical modality is on only when the computing device determines that the screen of the tissue using the first optical modality is inconclusive;
further interrogate the tissue using the second optical modality using the second optical analysis device;
analyze measurements of the tissue from the further interrogation of the tissue using the second optical modality using the second optical analysis device; and
control the display device to provide respective data relating to the measurements of the tissue obtained by one or more of the first optical modality and the second optical modality.

2. The system of claim 1, further comprising an optical coupling device configured to optically couple the optical probe to each of the one or more light sources, the first optical analysis device, and the second optical analysis device.

3. The system of claim 1, wherein the computing device is further configured to:
select the first optical modality for use at the optical probe; and,
use the first optical modality as a screen of the tissue to determine whether the tissue is healthy or not healthy; and, when the screen is inconclusive:
select the second optical modality for use at the optical probe; and,
use the second optical modality for further interrogation of the tissue.

4. The system of claim 1, wherein the computing device is further configured to, when the tissue is determined to be at a site of interest: control the second light source to be on to use the second optical modality for further interrogation of the tissue.

5. The system of claim 1, wherein the first optical modality is selected from a group consisting of Ultraviolet spectroscopy, visible spectroscopy, shortwave infrared spectroscopy, near infrared spectroscopy, broadband spectroscopy, optical coherence tomography (OCT), fluorescence spectroscopy, time-resolved fluorescence spectroscopy, and laser-induced breakdown spectroscopy (LIBS).

6. The system of claim 1, wherein the second optical modality is selected from a group consisting of Raman spectroscopy, surface enhanced Raman spectroscopy (SERS), stimulated Raman spectroscopy (SRS), and coherence anti-Stokes Raman spectroscopy (CARS).

7. The system of claim 1, further comprising one or more power sources for powering the one or more light sources, the first optical analysis device and the second optical analysis device.

8. The system of claim 1, wherein the optical probe comprises one or more optical fibers configured to convey the excitation light to the tissue and one or more further optical fibers configured to collect the light in the first wavelength range and the light in the second wavelength range from the tissue.

9. A method comprising:
positioning an optical probe to identify a region of interest;
controlling, using a computing device, during a surgery on tissue and when the optical probe is positioned to identify the region of interest, a first light source to be on and a second light source to be off, the first light source and the second light source being one or more light sources configured to provide excitation light, the first light source configured to emit light in a first wavelength range and the second light source configured to emit light in a second wavelength range, the computing device in communication with each of a first optical analysis device and a second optical analysis device, the one or more light sources, and a display device, the first optical analysis device configured to receive light in the first wavelength range and analyze the light in the first wavelength range using a first optical modality, a second optical analysis device configured to receive light in the second wavelength range and analyze the light in the second wavelength range using a second optical modality, the first optical modality having a faster acquisition time than the second optical modality, the second optical modality providing at least one of more detailed data and data with higher specificity, as compared to the first optical modality, regarding a nature of the tissue under analysis during the surgery using the first optical analysis device and the second optical analysis device, the excitation light being conveyed to tissue using the optical probe configured to receive the light in the first wavelength range from the tissue; and receive the light in the second wavelength range from the tissue, the excitation light being conveyed to the optical probe from the one or more light sources using a sample-interaction end of the optical probe comprising: excitation fiber optics configured to convey the excitation light from the one or more light sources to the optical probe; a first set of fiber optics configured to convey the light in the first wavelength range from the optical probe to the first optical analysis device; and a second set of fiber optics configured to convey the light in the second wavelength range from the optical probe to the second optical analysis device, a number the second set of fiber optics being more than a respective number of the first set of fiber optics;

screening, at the computing device, the tissue according to the first optical modality using the first optical analysis device to determine whether the tissue is healthy or not healthy;

when the screening of the tissue using the first optical modality is determined to be inconclusive, wherein determining that the screen is inconclusive occurs when a measurement of the tissue using the first optical modality has a margin of error that is above a threshold margin of error:
controlling, at the computing device, the first light source to remain on;
controlling, at the computing device, the second light source to be on, such that the second optical modality is on only when the computing device determines that the screen of the tissue using the first optical modality is inconclusive;
further interrogating the tissue using the second optical;
analyzing, via the computing device, measurements of the tissue from the further interrogating of the tissue using the second optical modality using the second optical analysis device; and
controlling, using the computing device, the display device to provide respective data relating to the measurements of the tissue obtained by one or more of the first optical modality and the second optical modality.

10. The method of claim 9, further comprising determining whether the tissue is healthy or not healthy by:
comparing one or more of a collected spectrum respective to the first optical modality and collected data respective to the first optical modality to one or more of reference spectra and reference data respective to one or more of healthy tissue and unhealthy tissue;
when one or more the collected spectrum and the collected data matches one or more of a healthy tissue reference spectra and healthy tissue reference data within a first given margin of error, determining that the tissue is healthy; and,
when one or more the collected spectrum and the collected data matches one or more of an unhealthy tissue reference spectra and unhealthy tissue reference data within a second given margin of error, determining that the tissue is unhealthy.

11. The method of claim 9, further comprising determining whether the screen is inconclusive by:
comparing one or more of a collected spectrum respective to the first optical modality and collected data respective to the first optical modality to one or more of reference spectra and reference data respective to one or more of healthy tissue and unhealthy tissue; and,
when one or more the collected spectrum and the collected data does not match one or more of the reference spectra and the reference data within at least one given margin of error, determining that the screen is inconclusive.

12. The method of claim 9, wherein the first optical modality is selected from a group consisting of Ultraviolet spectroscopy, visible spectroscopy, shortwave infrared spectroscopy, near infrared spectroscopy, broadband spectroscopy, optical coherence tomography (OCT), fluorescence spectroscopy, time-resolved fluorescence spectroscopy, and laser-induced breakdown spectroscopy (LIBS).

13. The method of claim 9, wherein the second optical modality is selected from a group consisting of Raman spectroscopy, surface enhanced Raman spectroscopy (SERS), stimulated Raman spectroscopy (SRS), and coherence anti-Stokes Raman spectroscopy (CARS).

* * * * *